(12) United States Patent
Zhan et al.

(10) Patent No.: US 11,644,587 B2
(45) Date of Patent: May 9, 2023

(54) PIXEL SUMMING SCHEME AND METHODS FOR MATERIAL DECOMPOSITION CALIBRATION IN A FULL SIZE PHOTON COUNTING COMPUTED TOMOGRAPHY SYSTEM

(71) Applicant: CANON MEDICAL SYSTEMS CORPORATION, Otawara (JP)

(72) Inventors: Xiaohui Zhan, Vernon Hills, IL (US); Xiaofeng Niu, Vernon Hills, IL (US)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 306 days.

(21) Appl. No.: 17/153,524

(22) Filed: Jan. 20, 2021

(65) Prior Publication Data
US 2022/0229196 A1 Jul. 21, 2022

(51) Int. Cl.
G01N 23/00 (2006.01)
A61B 6/00 (2006.01)
G01T 7/00 (2006.01)
G01N 23/046 (2018.01)
G01T 1/20 (2006.01)
G06T 7/00 (2017.01)
A61B 6/03 (2006.01)

(52) U.S. Cl.
CPC .............. G01T 7/005 (2013.01); A61B 6/035 (2013.01); A61B 6/4241 (2013.01); G01N 23/046 (2013.01); G01T 1/20184 (2020.05); G06T 7/0012 (2013.01); *G01N 2223/303* (2013.01); *G01N 2223/5055* (2013.01); *G06T 2207/10081* (2013.01); *G06T 2207/30168* (2013.01)

(58) Field of Classification Search
CPC ....... A61B 6/4241; A61B 6/482; A61B 6/583; A61B 6/585; A61B 6/035; G01N 2223/303; G01N 23/046
See application file for complete search history.

(56) References Cited

U.S. PATENT DOCUMENTS

| 2014/0233693 | A1 | 8/2014 | Wang et al. |
| 2017/0332984 | A1 | 11/2017 | Brendel et al. |
| 2019/0313993 | A1* | 10/2019 | Zhou ...................... A61B 6/032 |

OTHER PUBLICATIONS

Kun Yang et al.; "A practical calibration criterion for image-based material decomposition in spectral computed tomography", Alexandria University, Alexandria Engineering Journal, Mar. 7, 2020.

* cited by examiner

*Primary Examiner* — Dani Fox
(74) *Attorney, Agent, or Firm* — Oblon, McClelland, Maier & Neustadt, L.L.P.

(57) ABSTRACT

A method and a system for a two-step calibration method for the polychromatic semiconductor-based PCD forward counting model, to account for various pixel summing readout modes for imaging at different resolutions. The flux independent weighted bin response function is estimated using the expectation maximization method, and then used to estimate the pileup correction terms at plural tube voltage settings for each detector pixel. To correct the variation of the detector response due to different PCD sub-pixel summing schemes, the embodiments calibrate forward model parameters based on the various pixel readout modes.

20 Claims, 8 Drawing Sheets

PIXEL SUMMING SCHEME AND METHODS FOR MATERIAL DECOMPOSITION CALIBRATION IN A FULL SIZE PHOTON COUNTING COMPUTED TOMOGRAPHY SYSTEM

BACKGROUND

Technical Field

The disclosure relates to material decomposition in a full size photon counting computed tomography system.

DESCRIPTION OF THE RELATED ART

Computed tomography (CT) systems and methods are typically used for medical imaging and diagnosis. CT systems generally create projection images through a subject's body at a series of projection angles. A radiation source, such as an X-ray tube, irradiates the body of a subject and projection images are generated at different angles. Images of the subject's body can be reconstructed from the projection images.

Conventionally, energy-integrating detectors (EIDs) and/or photon-counting detectors (PCDs) have been used to measure CT projection data. PCDs offer many advantages including their capacity for performing spectral CT, wherein the PCDs resolve the counts of incident X-rays into spectral components referred to as energy bins, such that collectively the energy bins span the energy spectrum of the X-ray beam. Unlike non-spectral CT, spectral CT generates information due to different materials exhibiting different X-ray attenuation as a function of the X-ray energy. These differences enable a decomposition of the spectrally resolved projection data into different material components, for example, the two material components of the material decomposition can be bone and water.

Even though PCDs have fast response times, at high X-ray flux rates indicative of clinical X-ray imaging, multiple X-ray detection events on a single detector may occur within the detector's time response, a phenomenon called pileup. Left uncorrected, pileup effect distorts the PCD energy response and can degrade reconstructed images from PCDs. When these effects are corrected, spectral CT has many advantages over conventional CT. Many clinical applications can benefit from spectral CT technology, including improved material differentiation since spectral CT extracts complete tissue characterization information from an imaged object.

One challenge for more effectively using semiconductor-based PCDs for spectral CT is performing the material decomposition of the projection data in a robust and efficient manner. For example, correction of pileup in the detection process can be imperfect, and these imperfections degrade the material components resulting from the material decomposition.

In a photon counting CT system, the semiconductor-based detector using direct conversion is designed to resolve the energy of the individual incoming photons and generate measurement of multiple energy bin counts for each integration period. However, due to the detection physics in such semiconductor materials (e.g., CdTe/CZT), the detector energy response is largely degraded/distorted by charge sharing, k-escape, and scattering effects in the energy deposition and charge induction process, as well as electronic noise in the associated front-end electronics. Due to finite signal induction time, at high count-rate conditions, pulse pile-up also distorts the energy response.

Due to sensor material non-uniformity and complexity of the integrated detection system, it is very difficult to do accurate modeling of such detector response for a photon-counting detector just based on physics theories or Monte Carlo simulations that are based on certain modeling of the signal induction process, which determines the accuracy of the forward model of each measurement. Also, due to uncertainties in the incident X-ray tube spectrum modeling, additional errors in the forward model are introduced, and all these factors eventually degrade the material decomposition accuracy from the PCD measurements, therefore the generated spectral image quality.

Calibration methods have been proposed to solve such problems in the literature. The general idea is to use multiple transmission measurements of various known path lengths to calibrate the forward model such that it agrees with the calibration measurements. Some ideas are applied on estimation of the X-ray spectrum in conventional CT, see Sidky et al., Journal of Applied Physics 97(12), 124701 (2005) and Duan et al., Medical Physics 38(2), February, 2011, and later adopted on PCD measurements to estimate the combined system spectral response, see Dickmann et al., Proc. SPIE 10573, Medical Imaging 2018: Physics of Medical Imaging, 1057311 (Mar. 9, 2018). However, there can be many variations in the detail design and implementation of the calibration method, especially considering the application feasibility in a full 3rd generation CT geometry, which has not been demonstrated or documented in the literature so far.

For a typical semiconductor based PCD, the detector usually features a pixelated design, which uses smaller sub-pixels in group as equivalent to a conventional pixel size. This enables high-resolution imaging with smaller pixel sizes, but also requires different calibration schemes with various pixel patterns. Here, the disclosure is focused on the pixelated pattern design of the detector and weighting methods for material decomposition calibration.

SUMMARY

The embodiments presented herein relate to a two-step calibration method for the polychromatic semiconductor based PCD forward counting model, to account for various pixel summing readout modes for imaging at different resolutions. The method consists of two parts: 1) estimation of the flux independent weighted bin response function $S_{wb}(E)$ using the expectation maximization (EM) method, and 2) estimation of the pileup correction term $P_b(E, N_b, N_{tot})$. Once $S_{wb}(E)$ is estimated from the calibration at plural tube voltage (kVp) settings for each detector pixel, it is saved as a software calibration table in the system. It is then used as an input to estimate the pileup correction terms $P_b(E, N_b, N_{tot})$ at higher flux scans. Both tables are then used for the material decomposition in operational scans to estimate the basis material path lengths.

To correct the variation of the detector response due to different PCD sub-pixel summing schemes, the embodiments calibrate forward model parameters based on the various pixel readout modes.

Each sub-pixel (or a combined pixel composed of a plurality of sub-pixels) is calibrated separately following the same calibration and processing workflow. This applies to all the air or object scans used to calibrate the forward model and the patient/object scans that use the different pixel readout schemes for imaging with the calibrated tables.

To correct anti-scatter grid (ASG) shadow differences on different sub-pixels or combined pixels at different rotation speeds, the calibration is performed at each supported rotation speed as well.

BRIEF DESCRIPTION OF THE DRAWINGS

The application will be better understood in light of the description which is given in a non-limiting manner, accompanied by the attached drawings in which.

DETAILED DESCRIPTION OF THE PREFERRED EMBODIMENTS

Reference throughout this specification to "one embodiment" or "an embodiment" means that a particular feature, structure, material, or characteristic described in connection with the embodiment is included in at least one embodiment of the application, but do not denote that they are present in every embodiment.

Thus, the appearances of the phrases "in one embodiment" or "in an embodiment" in various places throughout this specification are not necessarily referring to the same embodiment of the application. Furthermore, the particular features, structures, materials, or characteristics may be combined in any suitable manner in one or more embodiments.

Figure 1:
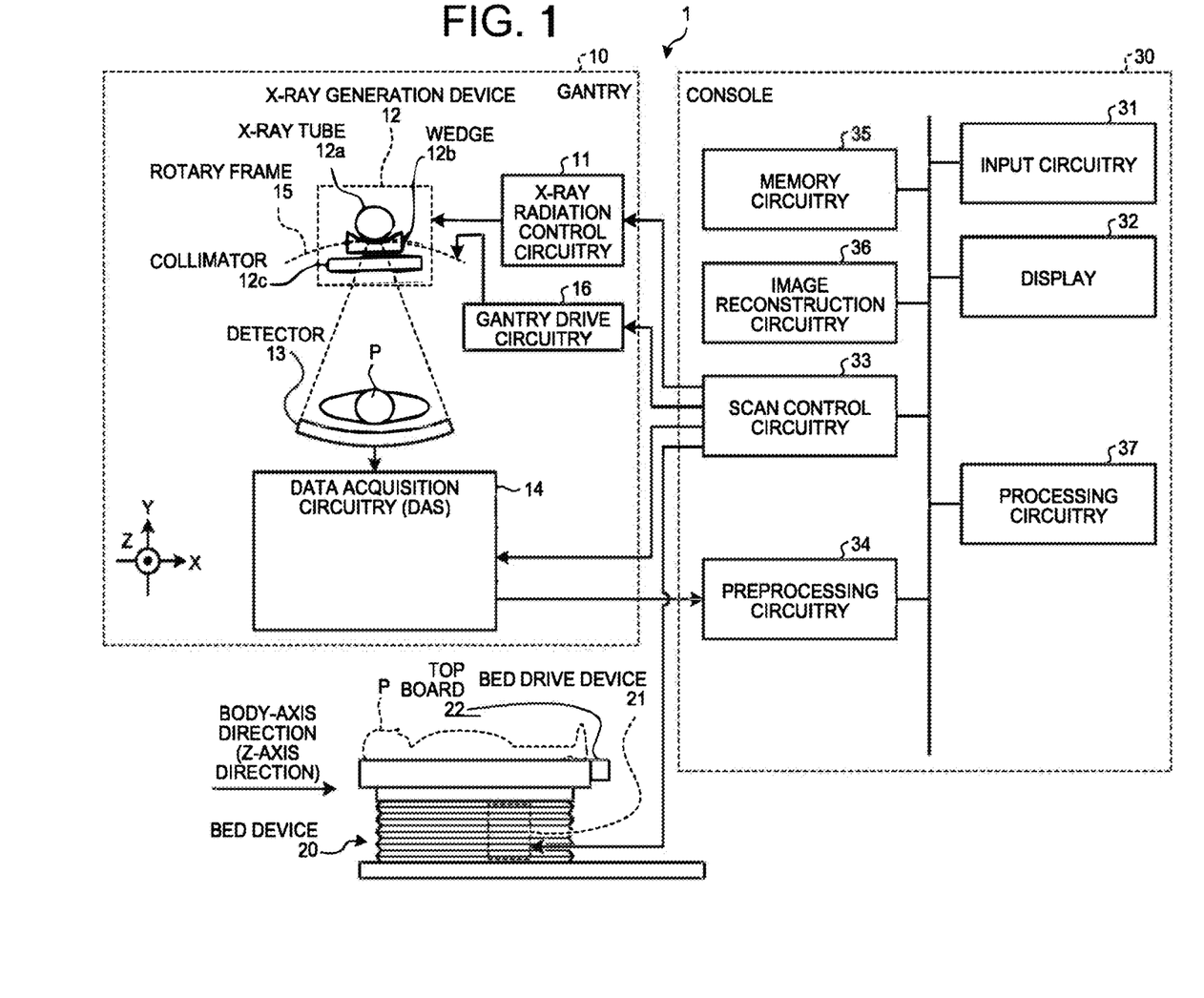
FIG. 1 shows an example of the configuration of a photon-counting type X-ray CT apparatus.

FIG. 1 is a diagram that illustrates an example of the configuration of a photon-counting type X-ray CT apparatus 1. As illustrated in FIG. 1, the photon-counting type X-ray CT apparatus 1 includes a gantry 10, a bed device 20, and a console 30.

The gantry 10 is a device that emits X-rays to a subject P (patient), detects the X-rays that are transmitted through the subject P, and outputs them to the console 30, and it includes X-ray radiation control circuitry 11, an X-ray generation device 12, a detector 13, data acquisition circuitry (DAS: Data Acquisition System) 14, a rotary frame 15, and gantry drive circuitry 16.

The rotary frame 15 is an annular frame that supports the X-ray generation device 12 and the detector 13 such that they are opposed to each other with the subject P interposed therebetween and that is rotated at high speed in a circular orbit around the subject P by the gantry drive circuitry 16.

The X-ray radiation control circuitry 11 is a device that serves as a high-voltage generation unit and supplies a high voltage to an X-ray tube 12a, and the X-ray tube 12a generates X-rays by using the high voltage that is supplied from the X-ray radiation control circuitry 11. Under the control of scan control circuitry 33, the X-ray radiation control circuitry 11 adjusts the tube voltage or the tube current that is supplied to the X-ray tube 12a, thereby adjusting the amount of X-rays that are emitted to the subject P.

Furthermore, the X-ray radiation control circuitry 11 switches a wedge 12b. Furthermore, the X-ray radiation control circuitry 11 adjusts the numerical aperture of a collimator 12c, thereby adjusting the radiation range (the fan angle or the cone angle) of X-rays. Moreover, there may be a case where multiple types of wedges are manually switched by an operator.

The X-ray generation device 12 is a device that generates X-rays and emits the generated X-rays to the subject P, and it includes the X-ray tube 12a, the wedge 12b, and the collimator 12c.

The X-ray tube 12a is a vacuum tube that emits X-ray beams to the subject P by using the high voltage that is supplied by the X-ray radiation control circuitry 11, and it emits X-ray beams to the subject P in accordance with the rotation of the rotary frame 15. The X-ray tube 12a generates X-ray beams that spread with the fan angle and the cone angle. For example, under the control of the X-ray radiation control circuitry 11, the X-ray tube 12a is capable of continuously emitting X-rays all around the subject P for a full reconstruction or continuously emitting X-rays for a half reconstruction within an emission range (180°+the fan angle) that enables a half reconstruction. Furthermore, under the control of the X-ray radiation control circuitry 11, the X-ray tube 12a is capable of intermittently emitting X-rays (pulse X-rays) at a previously set position (tube position). Furthermore, the X-ray radiation control circuitry 11 is capable of changing the intensity of X-rays, emitted from the X-ray tube 12a. For example, the X-ray radiation control circuitry 11 increases the intensity of X-rays, emitted from the X-ray tube 12a, at a specific tube position, and it decreases the intensity of X-rays, emitted from the X-ray tube 12a, in the area other than the specific tube position.

The wedge 12b is an X-ray filter that adjusts the amount of X-rays with regard to the X-rays that are emitted from the X-ray tube 12a. Specifically, the wedge 12b is a filter that transmits and attenuates X-rays, emitted from the X-ray tube 12a, such that X-rays, emitted from the X-ray tube 12a to the subject P, has a predetermined distribution. For example, the wedge 12b is a filter that is obtained by processing aluminum so as to have a predetermined target angle or a predetermined thickness. Furthermore, the wedge is also called a wedge filter or a bow-tie filter.

The collimator 12c is a slit that narrows the irradiation range of X-rays, of which the amount of X-rays has been adjusted by the wedge 12b, under the control of the X-ray radiation control circuitry 11.

The gantry drive circuitry 16 drives and rotates the rotary frame 15 so that the X-ray generation device 12 and the detector 13 are rotated in a circular orbit around the subject P.

Each time an X-ray photon enters, the detector 13 outputs the signal with which the energy value of the X-ray photon may be measured. The X-ray photon is, for example, an X-ray photon that is emitted from the X-ray tube 12a and is transmitted through the subject P. The detector 13 includes multiple detection elements that output an electric signal (analog signal) of 1 pulse each time an X-ray photon enters. The photon-counting type X-ray CT apparatus 1 counts the number of electric signals (pulses) so as to count the number of X-ray photons that enter each of the detection elements.

Furthermore, the photon-counting type X-ray CT apparatus 1 performs arithmetic processing on the signal so as to measure the energy value of the X-ray photon that causes output of the signal.

The above-described detection element includes, for example, a scintillator and an optical sensor, such as a photomultiplier tube. In such a case, the detector 13, illustrated in FIG. 1, is an indirect-conversion type detector that converts the incident X-ray photon into scintillator light by using the scintillator and converts the scintillator light into an electric signal by using the optical sensor, such as a photomultiplier tube. Furthermore, there may be a case where the above-described detection element is a semiconductor device of, for example, cadmium telluride (CdTe), cadmium zinc telluride (CdZnTe), or the like. In such a case, the detector 13, illustrated in FIG. 1, is a direct-conversion type detector that directly converts the incident X-ray photon into an electric signal.

For example, the detector 13, illustrated in FIG. 1, is a plane detector in which detection elements are arranged in N columns in the channel direction (the direction of the X axis in FIG. 1) and in M columns in the direction of the rotational center axis of the rotary frame 15 (the direction of the Z axis in FIG. 1) where the gantry 10 is not tilted. When a photon enters, the detection element outputs an electric signal of one pulse. The photon-counting type X-ray CT apparatus 1 discriminates among individual pulses that are output from a detection element 131, thereby counting the number of X-ray photons that enter the detection element 131. Furthermore, the photon-counting type X-ray CT apparatus 1 performs arithmetic processing based on the intensity of a pulse, thereby measuring the energy value of the counted X-ray photon.

The data acquisition circuitry 14 is a data acquisition system (DAS), and it acquires the detection data on X-rays that are detected by the detector 13. For example, the data acquisition circuitry 14 generates the count data that is obtained by counting the photons (X-ray photons), which come from the X-ray that is transmitted through the subject, for each energy band, and it transmits the generated count data to the console 30 that is described later. For example, if X-rays are continuously emitted from the X-ray tube 12a while the rotary frame 15 is rotated, the data acquisition circuitry 14 acquires the group of count data for the entire periphery (360 degrees). The data acquisition circuitry 14 also can acquire data for each view. Furthermore, the data acquisition circuitry 14 transmits each acquired count data in relation to the tube position to the console 30 that is described later. The tube position is the information that indicates the projection direction of the count data.

The bed device 20 is a device on which the subject P is placed and, as illustrated in FIG. 1, it includes a bed drive device 21 and a top board 22. The bed drive device 21 moves the top board 22 in the direction of the Z axis to move the subject P into the rotary frame 15. The top board 22 is a board on which the subject P is placed. Furthermore, in the present embodiment, an explanation is given of a case where the relative position between the gantry 10 and the top board 22 is changed by controlling the top board 22; however, this is not a limitation on the embodiment. For example, if the gantry 10 is self-propelling, the relative position between the gantry 10 and the top board 22 may be changed by controlling driving of the gantry 10.

Furthermore, for example, the gantry 10 conducts helical scan to scan the subject P in a helical fashion by rotating the rotary frame 15 while the top board 22 is moved. Alternatively, the gantry 10 conducts conventional scan to scan the subject P in a circular orbit by rotating the rotary frame 15 with the position of the subject P fixed after the top board 22 is moved. Alternatively, the gantry 10 implements a step-and-shoot method to conduct conventional scan at multiple scan areas by moving the position of the top board 22 at a constant interval.

The console 30 is a device that receives an operation of the photon-counting type X-ray CT apparatus 1 from an operator and that reconstructs X-ray CT image data by using the projection data that is acquired by the gantry 10. As illustrated in FIG. 1, the console 30 includes input circuitry 31, a display 32, the scan control circuitry 33, preprocessing circuitry 34, memory circuitry 35, image reconstruction circuitry 36, and processing circuitry 37.

The input circuitry 31 includes a mouse, keyboard, trackball, switch, button, joystick, or the like, which is used by an operator of the photon-counting type X-ray CT apparatus 1 to input various commands or various settings, and it transfers the information on the command or setting, received from the operator, to the processing circuitry 37. For example, the input circuitry 31 receives, from an operator, a capturing condition for X-ray CT image data, a reconstruction condition for reconstructing X-ray CT image data, an image processing condition for X-ray CT image data, or the like.

The display 32 is a monitor that is viewed by an operator and, under the control of the processing circuitry 37, it displays the image data, generated from X-ray CT image data, to the operator or displays a graphical user interface (GUI) for receiving various commands, various settings, or the like, from the operator via the input circuitry 31.

The scan control circuitry 33 controls operations of the X-ray radiation control circuitry 11, the gantry drive circuitry 16, the data acquisition circuitry 14, and the bed drive device 21 under the control of the processing circuitry 37, thereby controlling data acquisition processing by the gantry 10. For example, scan control circuitry 33 sends sequence control commands to data acquisition circuitry 14 to control exposure operations, as discussed in more detail below.

The preprocessing circuitry 34 performs correction processing, such as logarithmic conversion processing, offset correction, sensitivity correction, or beam hardening correction, on the count data that is generated by the data acquisition circuitry 14, thereby generating corrected projection data.

The memory circuitry 35 stores the projection data that is generated by the preprocessing circuitry 34. Furthermore, the memory circuitry 35 stores the image data, or the like, which is generated by the image reconstruction circuitry 36 that is described later. Moreover, the memory circuitry 35 appropriately stores processing results of the processing circuitry 37 that is described later.

The image reconstruction circuitry 36 reconstructs X-ray CT image data by using the projection data that is stored in the memory circuitry 35. Here, the reconstruction method includes various methods, and it may be, for example, back projection processing. Furthermore, the back projection processing may include, for example, back projection processing by using a filtered back projection (FBP) method. Alternatively, the image reconstruction circuitry 36 may also use a successive approximation technique to reconstruct X-ray CT image data. Furthermore, the image reconstruction circuitry 36 conducts various types of image processing on X-ray CT image data, thereby generating image data. Then, the image reconstruction circuitry 36 stores, in the memory circuitry 35, the reconstructed X-ray CT image data or the image data that is generated during various types of image processing.

The processing circuitry 37 controls operations of the gantry 10, the bed device 20, and the console 30 so as to perform the overall control on the photon-counting type X-ray CT apparatus 1. Specifically, the processing circuitry 37 controls the scan control circuitry 33 so as to control CT scan that is conducted by the gantry 10. Furthermore, the processing circuitry 37 controls the image reconstruction circuitry 36 so as to control image reconstruction processing or image generation processing by the console 30. Furthermore, the processing circuitry 37 performs control such that various types of image data, stored in the memory circuitry 35, are displayed on the display 32.

Heretofore, the overall configuration of the photon-counting type X-ray CT apparatus 1 according to the first embodiment is explained. Here, each processing function, performed by each of the above-described circuitry, is stored in the memory circuitry 35 in the form of the program that is executable by the computer. Furthermore, each circuitry reads and executes each program from the memory circuitry 35, thereby performing the above-described various functions.

In one example, programs corresponding to the operations of the data acquisition circuitry 14 are stored in the memory circuitry 35 in the form of a program that is executable by a computer. Processor 37 executes the programs for data acquisition circuitry 14 and sends instructions to and controls data acquisition circuitry 14 to acquire data as well as controls the transfer data from data acquisition circuitry 14. In a second example, data acquisition circuitry 14 includes a processor that reads and executes each program from the memory circuitry 35 to implement the function that corresponds to each program.

Furthermore, the word "processor", used in the above explanations, means for example a central processing unit (CPU), a graphics processing unit (GPU), or a circuit, such as an application specific integrated circuit (ASIC), or a programmable logic device (e.g., a simple programmable logic device: SPLD, a complex programmable logic device: CPLD, or a field programmable gate array: FPGA). The processor reads and executes the program, stored in the memory circuitry, to perform the function. Furthermore, a configuration may be such that, instead of storing a program in the memory circuitry, a program is directly installed in a circuit of the processor. In this case, the processor reads and executes the program, installed in the circuit, to perform the function. Furthermore, with regard to the processors according to the present embodiment, instead of the case where each processor is configured as a single circuit, multiple independent circuits may be combined to be configured as a single processor to implement the function.

Figure 2:
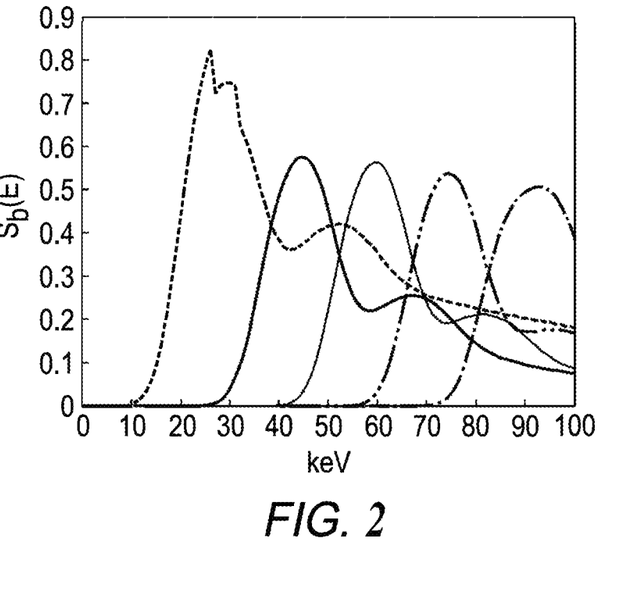
FIG. 2 shows an example of a PCD bin response function $S_b(E)$ for a photon counting detector. Each curve stands for an example function for each energy bin.

In a transmission measurement using a photon counting energy-resolving detector (PCD), the forward model can be formulated as below:

$$N_b(l_1,\ldots,l_M) = N_0 \times \int dE\, w(E) S_b(E) \exp(-\Sigma \mu_m l_m) \tag{1}$$

where, $S_b(E)$ stands for the bin response function defined as $S_b(E) = \int_{E_{bL}}^{E_{bH}} dE'\, R(E, E')$, and $R(E, E')$ is the detector response function, and $E_{bL}$ and $E_{bH}$ are the low and high energy thresholds of each counting bin. FIG. 2 shows an example model of a typical $S_b(E)$ for a photon counting detector, where a long tail above the energy window is induced by charge sharing, k-escape and scattering effect. The low energy tail is mostly due to the finite energy resolution from the associated electronic noise. $N_0$ is the total flux from an air scan, $\mu_m$ and $l_m$ are the $m^{th}$ basis material linear attenuation coefficient and path length, respectively. $w(E)$ is the normalized incident X-ray spectrum. In practise, both $w(E)$ and $S_b(E)$ are not exactly known, and they can be combined as one term $S_{wb}(E) = w(E) S_b(E)$, called thereafter the weighted bin response function. If $S_{wb}(E)$ can be calibrated through measurements, the decomposition problem at low flux conditions can be well solved.

For a high flux scan condition (e.g. a few percent of pulse pileup), pulse pileup introduces additional spectral distortion in the measurement. One way to correct for the pileup effect is to introduce additional correction terms (e.g. Dickmann uses the measured count rate(s) as input). And this type of additional calibration is based on an accurate estimation of the flux independent weighted bin response $S_{wb}(E)$.

In typical CT clinical scan conditions, it is common to encounter a few percent or higher pulse pileup for some measurements. The resulting effect is that material decomposition depends on the measured spectrum as well as the flux.

For a semiconductor-based PCD, the small pixel design is usually used, in which a smallest readout unit can be grouped into different patterns for the summed readout, and used for imaging at different resolutions. For different pixel summing schemes, the detector response is varied as the charge sharing and cross-talk effect are slightly different due to the different combined-pixel size and shape resulting from the sub-pixel size and shape. Therefore, the calibration and data processing need to account for this variation for more accurate material decomposition results.

For a $3^{rd}$ generation CT system, an ASG is often installed to reject scattered photons for cleaner measurements and better image quality. For this small detector pixel design in Photon-counting computed tomography (PCCT), in theory there is no dead detection area like in the conventional scintillator-based detectors, and one can employ the same ASG design or a different one to achieve optimal performance. If the same ASG design is used, then the ASG would produce different shadows across the sub-pixels, introducing even larger difference in the charge sharing and cross-talk effect (see FIG. 3). Hence, it is necessary to consider this variation factor in the forward model calibration as well.

Figure 3:
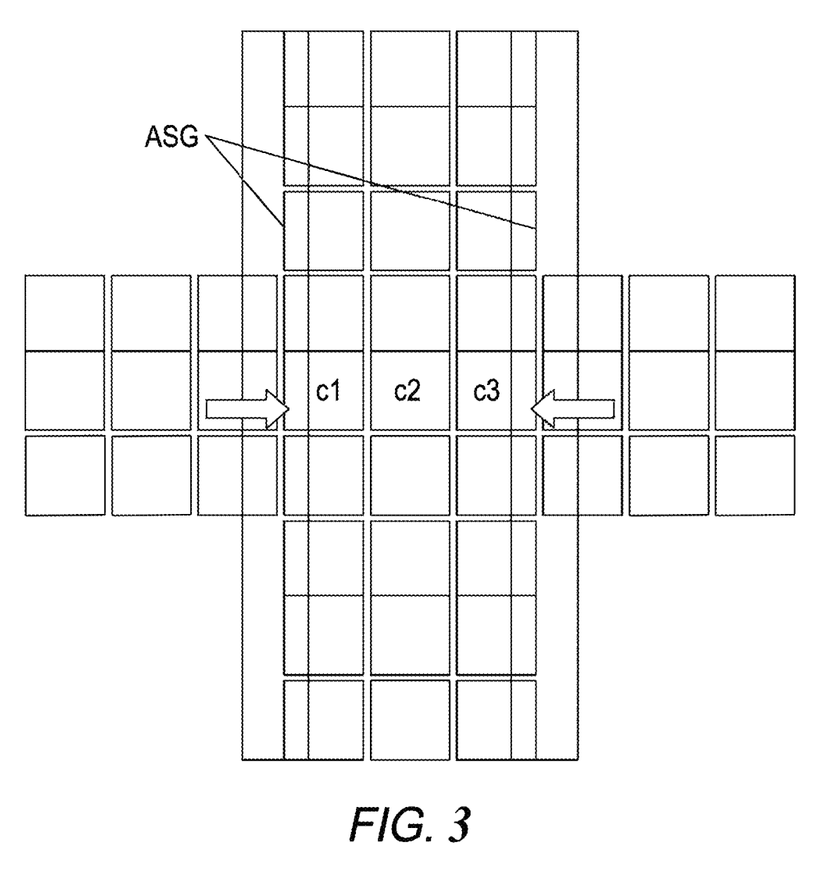
FIG. 3 shows an example of a 3×3 sub-pixel pattern with a one dimensional anti-scatter grid.

In particular, FIG. 3 shows an example of a 3×3 sub-pixel pattern with 1D ASGs that form a combined pixel. However, different sized sub-pixel patterns can be used, such as n×m sub-pixel patterns or n×n sub-pixels patterns generally where n>=2. For columns c1 and c3, due to the blocked area under ASG plates, the charge sharing and cross-talk effect is greatly reduced from the left/right side, making the effective detector response different from that at the center column c2.

The disclosure presented herein comprises a two-step calibration method for the PCD forward model for material decomposition. It consists of two parts: 1) estimation of the flux independent weighted bin response function $S_{wb}(E)$ using expectation maximization (EM) method and 2) estimation of the pileup correction term $P_b(E, N_b, N_{tot})$ which is a function of energy (E) and the measured bin counts ($N_b$, $N_{tot}$), where $N_b$ is the individual bin count and $N_{tot}$ is the total count of all the energy bins. The calibrated forward model can be expressed as:

$$N_b(l_1,\ldots,) = N_0 \int dE\, S_{wb}(E) * P_b(E, N_b, N_{tot}) \exp(-\Sigma \mu_m l_m) \tag{2}$$

A series of slab measurements with known materials and path lengths are used to calibrate the above forward model.

Here, instead of using only two materials, as in prior arts (e.g., see Dickmann), the method uses 2-5 different materials such as polypropylene, water, aluminium, titanium/copper, and k-edge materials to calibrate the weighted bin response function $S_{wb}(E)$ at low flux. With more selective materials used in the calibration, the number of total path lengths is reduced to achieve equivalent or better results.

Step 1: With an appropriate tube spectrum modelling to capture the characteristic peaks in the incident spectrum, and a physical model to simulate the photon-counting detector spectral response, an initial guess of $S_{wb}(E)$ can be produced. By using the EM method (e.g., see Sidky), $S_{wb}(E)$ can be reliably estimated for this very ill-conditioned problem based on a few transmission measurements.

Here, $P_b(E, N_b, N_{tot})$ is assumed to be constant in Step 1. The calibrated forward model can be simplified to a system of linear equations $$N_b(l_1,\ldots,l_M) = N_0 \int_{Emin}^{Emax} dE S_{wb}(E) \exp(-\Sigma \mu l_m) \quad (3)$$

Usually, the number of data measurements (M) is much smaller than the number of unknowns ($E_{max}$). With the assumption of Poisson distribution of the data acquisition, an iterative EM algorithm can be derived to find the optimal estimation of the unknown energy bin response function $S_{wb}(E)$, as described below.

When estimating the bin response function using low flux data acquisition, the pileup effect correction $P_b$ is assumed to be a known term (e.g. constant). So, the model is simplified to $$N_b = N_0 \int dE S_{wb}(E)[\exp[-\Sigma \mu_m(E) l_m]] \quad (4)$$

Let $A^j(E) = \exp[-\Sigma \mu_m(E) l_m^j]$ represent the attenuated path length for j-th measurement. Thus, for each measurement j, we have $$N_b^j = N_0 \int dE S_{wb}(E) A^j(E) = N_0 \Sigma_E S_{wb}(E) A^j(E) \quad (5)$$

With M measurements, the data acquisition can be written in the matrix form below $$N_0 \begin{pmatrix} A^1(1) & \cdots & A^1(E_{max}) \\ \vdots & \ddots & \vdots \\ A^M(1) & \cdots & A^M(E_{max}) \end{pmatrix}_{M \times E_{max}} \cdot \begin{pmatrix} S_{wb}(1) \\ \vdots \\ S_{wb}(E_{max}) \end{pmatrix}_{E_{max} \times 1} = \begin{pmatrix} N_b^1 \\ \vdots \\ N_b^M \end{pmatrix}_{M \times 1}$$

or $A \cdot S_{wb} = N_b$

By applying the EM iterative algorithm, the $S_{wb}$ can be estimated by $$S_{wb}^{(k+1)} = S_{wb}^{(k)} \odot ((A^T \cdot (N_b \oslash (A \cdot S_{wb}^{(k)}))) \oslash (A^T \cdot 1)) \quad (6)$$

where
k: iteration number
·: matrix multiplication
⊙: element-wise multiplication
⊘: element-wise division
1: vector of ones with size of M×1
the updating formula for $S_{wb}(E)$ is given by $$S_{wb}^{(k+1)}(E) = S_{wb}^{(k)}(E) \frac{\Sigma_{j'} A^{j'}(E) \frac{N_b^{j'}}{\Sigma_{E'} A^{j'}(E') S_{wb}^{(k)}(E')}}{\Sigma_{j'} A^{j'}(E)} \quad (7)$$

Step 2: Once $S_{wb}(E)$ is estimated from the calibration at each tube voltage (kVp) setting for each detector pixel, it is saved as a software calibration table on the system. It will be used as an input to further estimate the pileup correction terms $P_b(E, N_b, N_{tot})$ at higher flux scans. Both tables are then used for the material decomposition in object/patient scans to estimate the basis material path lengths.

The calibration tables are updated from time to time based on the system/detector performance variations. This can also be designed as an iterative procedure. If the image quality is not good enough on a quality check phantom, this calibration process is repeated with the updated calibration tables from the last iteration as the initial guess.

Figure 4:
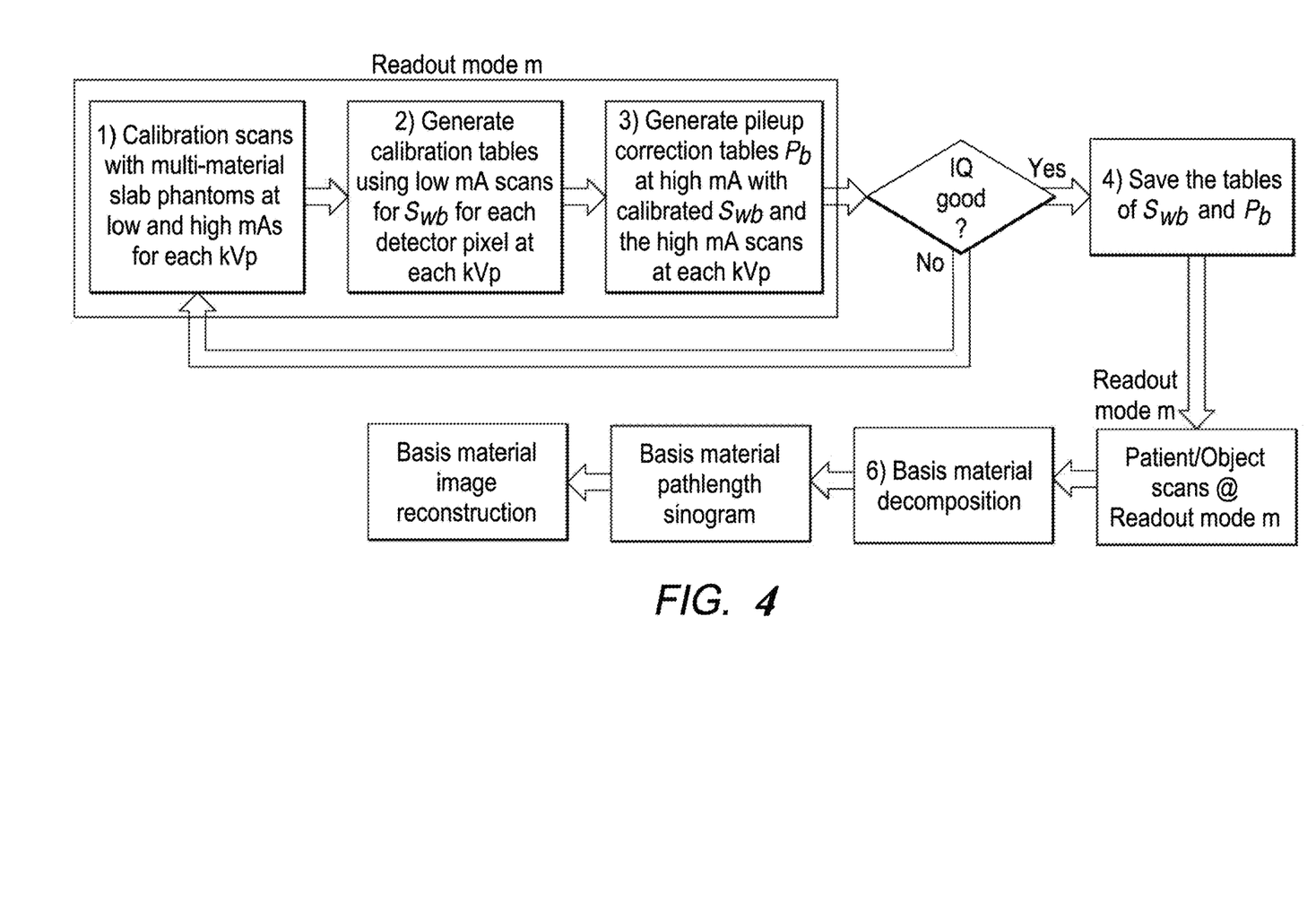
FIG. 4 shows a material decomposition calibration and processing workflow.

The high level workflow of the above process is demonstrated in FIG. 4. Steps 1) to 4) represent the calibration workflow, and steps 5) to 8) demonstrate how the calibration tables are used in the operational scans of patients/objects to produce spectral images.

First, a series of low flux scans on various material slabs are collected at each tube kVp setting, which is the peak potential applied on the X-ray tube. Typical CT systems support a few kVp settings from 70 to 140 kVp which generate different energy spectrums from the X-ray tube for different scan protocol. For a CT scan, both mA and kVp need to be pre-selected before the tube is turned on. Then, the low flux weighted bin response function $S_{wb}$ is estimated and with the estimated $S_{wb}$, the high flux slab scans are used to estimate the additional parameters in the pileup correction term $P_b$. With the estimation calibration tables of $S_{wb}$ and $P_b$ for each detector pixel, the quality of the calibration is checked on a quality phantom, e.g. a uniform water phantom, or phantom with multiple inserts with uniform known materials. The image quality is assessed with predefined standards, and if it is passed, the current calibration tables are saved and then used for the following patient/object scans data processing. Otherwise, the procedure goes through the first three steps again using the last iteration of $S_{wb}$ and $P_b$ as the initial guess. Here, commonly examined standards are: image CT number accuracy, uniformity, spatial resolution, noise and artifacts. To check the quality of this calibration, these metrics should all be checked, especially the accuracy and artifacts like ring or bands in the image, which indicate the calibration is not good enough.

Figure 5:
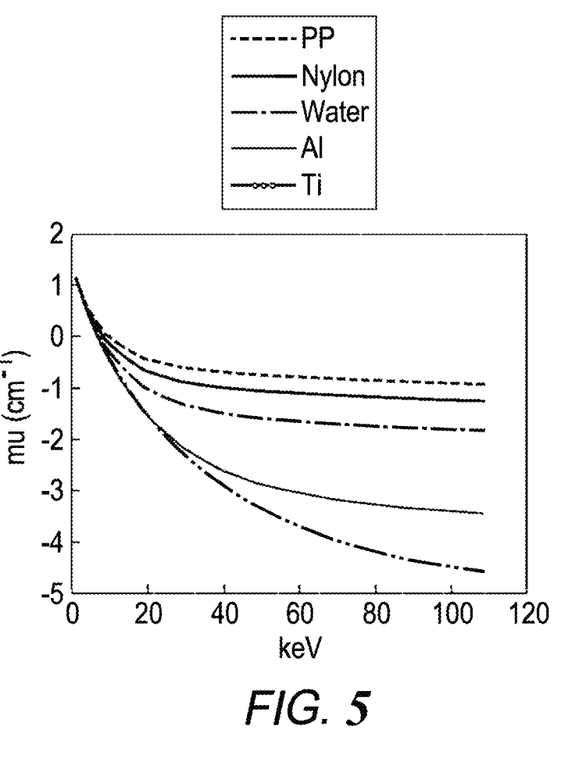
FIG. 5 shows normalized linear attenuation coefficients for different materials.

To choose the optimal materials and path lengths for this calibration, one can use the normalized linear attenuation coefficient vs. energy curves, see FIG. 5 to choose the ones that are different from each other, e.g. polypropylene, water, aluminum, titanium can be a good group of combinations for such calibrations which covers a large range of common materials present in human body.

In order to satisfy the low flux condition through the calibration measurement to minimize the pileup effect in the flow diagram, step 1, one can select to use nτ<x, where x~0.005-0.01 and n is the pixel count rate with the lowest tube flux setting, and τ is the effective dead time of the PCD Application Specific Integrated Circuit (ASIC). By satisfying this condition, one can calculate the shortest path length of each selected calibration material, and the rest of path lengths can either be selected by equal spacing in path length or in resulting measurement count rate.

Figure 6:
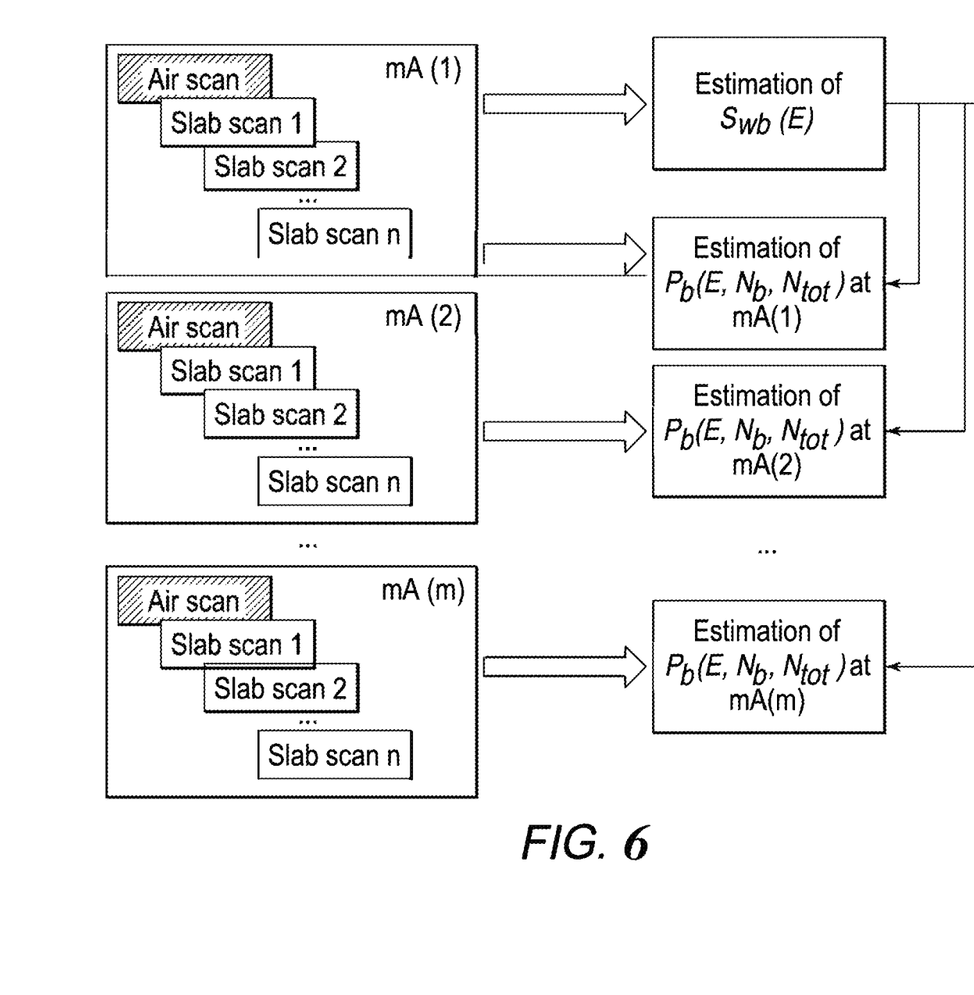
FIG. 6 shows a schematic of a calibration structure design, where the pileup correction tables $P_b$ are generated and used for each mA individually.
Figure 7:
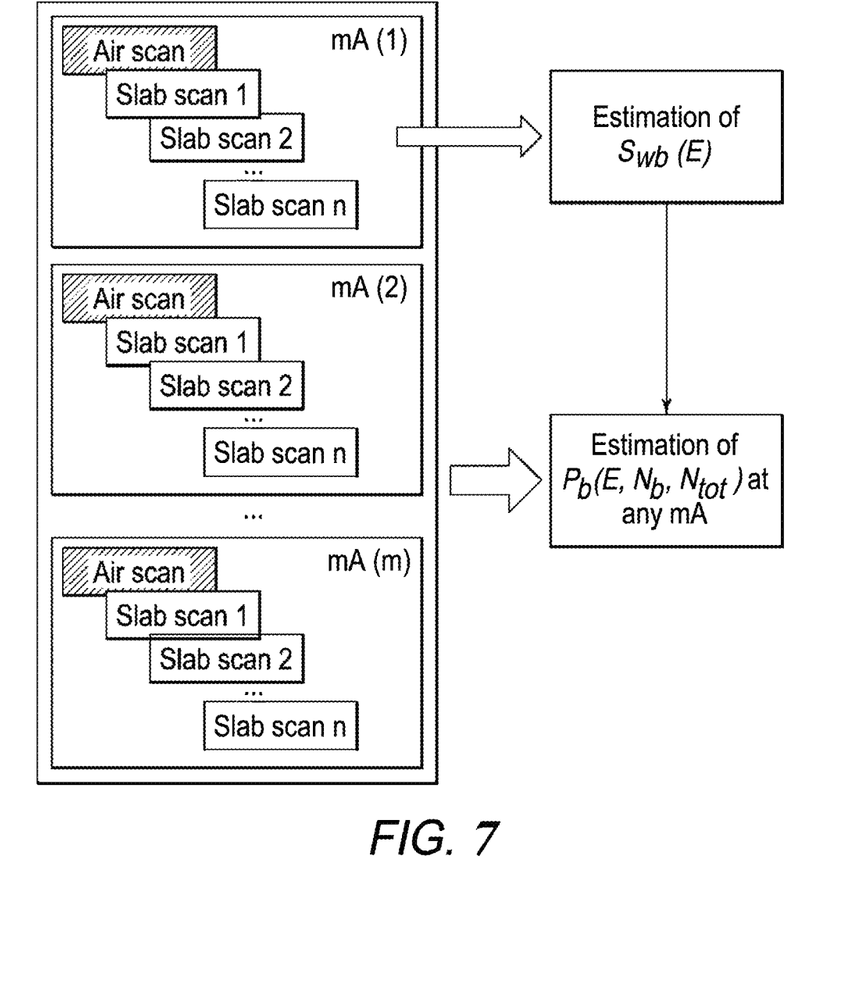
FIG. 7 shows a schematic of another calibration structure design, where a universal pileup correction table $P_b$ is generated for the entire mA range.
Figure 8A:
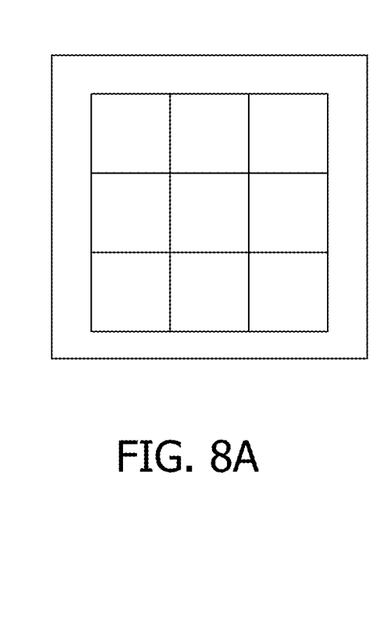
FIGS. 8A-8D show various summing schemes for decomposition calibration and processing.
Figure 8B:
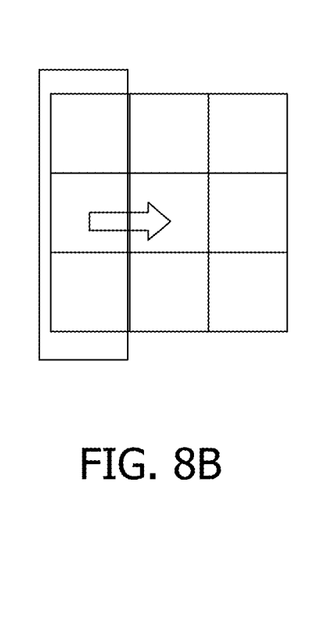
Figure 8C:
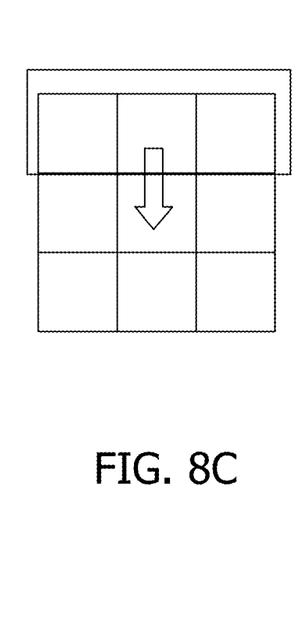
Figure 8D:
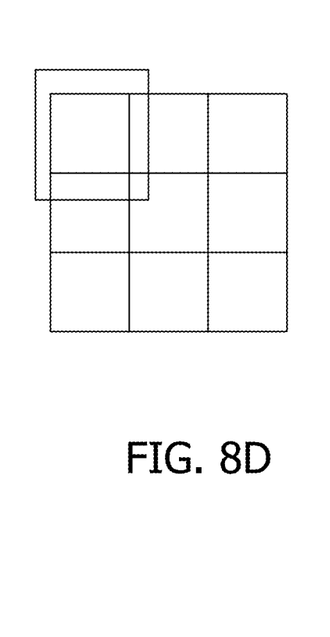

For calibration of the pileup correction term $P_b$ in step 3, the same slab material and path lengths are used for scans at high mA settings. The calibration data can be grouped for each mA and generate different correction tables for each mA setting (see FIG. 6), or include measurements at all flux ranges (e.g., from low to high mA, from high to low mA, or with most frequently used values first) to generate a universal correction table for a continuous mA setting (see FIG. 7).

The calibration measurements should be taken with sufficient statistics to minimize the influence of the statistical fluctuation. One non-limiting example is to use >1000 times more statistics as the typical integration period for the calibration data sets to minimize the transferred statistical error in the calibration. Each energy bin b of the calibration measurements will be used to update the corresponding $S_{wb}(E)$ and $P_b(E, N_b, N_{tot})$.

Since one can only do limited number of measurements with a few energy bins, the estimation is very ill-conditioned. In this case, a good initial guess is crucial for an accurate estimation as it provides additional constraints for the EM method. One of the design variations to accommodate non-ideal detectors is to allow a more flexible energy window for each bin in the initial guess of $S_b$, especially with small variations in the actual energy threshold setting of the ASIC. By setting the low threshold x keV lower, and high threshold y keV higher, the initial $S_b$ becomes:

$$S_b(E) = \int_{EbL-x}^{EbH+y} R(E,E')dE' \tag{8}$$

where x, y can be chosen between 5 to 10 keV to allow certain variations in the ASIC performance, while still providing additional constraints for the EM problem.

To capture the spectrum variation across the fan beam after bowtie filter and detector response variation across different detector pixels, this calibration process is done pixel by pixel with each bowtie/filter configuration.

The design described in the present application employs more than two materials in the calibration, which provides more sensitivity to constraint the weighted bin response function estimation problem of the photon counting detectors.

In addition, the method utilizes a different parameterization for the high flux pileup correction terms $P_b$ which is now a function of E, $N_b$ and $N_{tot}$. The total count term $N_{tot}$ is introduced for a better approximation of the true pileup phenomena, and can significantly improve the model capability at higher flux condition with fewer parameters.

Furthermore, various calibration path length ranges are used at different fan angles to improve the calibration accuracy and efficiency. The slab scans used for the forward model calibration can be selected based on the imaging task to generate the best image quality.

Finally, a different scheme is presented to calculate an initial guess of the weighted bin response function by enlarging the energy threshold window, to accommodate non-ideal detector/ASIC performance.

To accommodate various detector responses of different summing schemes with ASG, this disclosure presents calibration of the forward model with different sub-pixel summing schemes separately. The calibration tables for each pixel configuration are saved in digital data form and used accordingly in the data processing to reconstruct the images with different resolutions.

Steps 1) to 4) in FIG. 4 are repeated for different pixel readout summing modes. The calibration tables are saved for each mode and then applied for the patient/object scans with the same readout configuration.

In a semiconductor-based photon counting detector for CT, a pixel size between 200-500 μm is usually selected for optimal performance. It is a good balance between the charge sharing effect and pulse pileup under CT scan flux conditions. It is smaller than the typical conventional scintillator-based pixel which is usually ~1×1 mm. Therefore, the readout for image processing can have more than one modes, combining different number of sub-pixels into one or more combined pixels.

For the combined-pixel readout mode ($N_r \times N_c$) (i.e., the readout mode for a plurality of sub-pixels that have been combined), the forward model calibration can be done based on the measurement of the sum (or average) of the combined pixel:

$$N_b(\text{slab}) = \sum_r \sum_c N_b(r, c) \text{ slab}$$

$$N_b(\text{phantom}) = \sum_r \sum_c N_b(r, c)_{phantom}$$

FIGS. 8A-8D show examples of a 3∴3 sub-pixel scheme which forms a combined pixel equivalent to a conventional EID pixel. Four different summing schemes can be used for data readout: 3×3, 1×3, 3×1, 1×1, standing for four possible resolutions of the resulted image.

The disclosed calibration scheme for different pixel summing patterns for combined pixels are not limited to a specific sub-pixel pattern or a specific forward model, but can apply to any forward model calibration that is based on measurements of the known materials at different path length samples. Furthermore, the obtained counts for a sub-pixel pattern can be obtained such that an average over an entire sub-pixel pattern is obtained and a normalization factor, based on an estimate of anti-scatter grid (ASG) shadow on the sub-pixel pattern, is applied on the averaged counts.

FIGS. 8A-8D show various summing schemes for decomposition calibration and processing. In particular, in A), summing is performed over the combined pixel, e.g. a 3×3 summing mode. In B), summing is performed over the row direction, e.g. a 1×3 summing mode. In C), summing is performed over the channel direction, e.g. a 3×1 summing mode. Finally, in D), calibration is based on individual sub-pixel. The object scan material decomposition can choose to use one of the summing patterns with the corresponding calibrated tables.

By calibrating each sub-pixel and averaging the material decomposition results in the estimated path length sinogram for different combined readout modes, the disclosed method handles the averaging effect in the calibration process directly, avoiding complications in the data weighting after the decomposition step.

In order to reduce the calibration time, all the slab calibration data can be acquired using the smallest detector pixel unit (micro-pixel), then combined digitally into different summing patterns in the later on data processing, which can be either carried out in the front-end electronics, or detector/system firmware (FPGA).

Numerous modifications and variations of the embodiments presented herein are possible in light of the above teachings. It is therefore to be understood that within the scope of the claims, the disclosure may be practiced otherwise than as specifically described herein.

The invention claimed is:

1. A method for calibrating a response of a photon counting detector (PCD) for material decomposition in a photon counting computed tomography (CT) system, the method comprising:
   (1) performing, at a sub-pixel pattern of the PCD, a plurality of low flux scans comprising an air scan and scans using a plurality of slabs of different materials, at an initial current intensity and at plural tube voltage settings of an X-ray tube, for each scan, to obtain counts for each energy bin, and combining the obtained counts for the sub-pixel pattern;

(2) performing a basis material decomposition in object/patient scans to estimate the basis material based on the combined obtained counts of the sub-pixel pattern of (1).

2. The method according to claim 1, wherein the combining comprises summing performed over the entire sub-pixel pattern.

3. The method according to claim 1, wherein the combining comprises summing performed over a row direction or a channel direction of the sub-pixel pattern.

4. The method according to claim 1, further comprising estimating first parameters, which are dependent on energy, based on the combined obtained counts.

5. The method according to claim 4, further comprising estimating second parameters which are dependent on total counts of all energy bins, based on the estimated first parameters.

6. The method according to the claim 5, further comprising:
repeating, using each of the plurality of slabs, (1), estimating the first parameters, and estimating the second parameters for different current intensities other than the initial current intensity and at the same tube voltage to obtain the second parameters, respectively, for the different current intensities.

7. The method according to the claim 6, further comprising:
assessing image quality of a projection image by performing a phantom scan using the first parameters and the second parameters and if the quality of the projection image satisfies predefined standards, the first parameters and the second parameters are used for the basis material decomposition in object/patient scans to estimate the basis material.

8. The method according to the claim 6, wherein an initial guess of the first parameters is based on detector response function and low and high energy threshold of each counting bin, respectively.

9. The method according to claim 4, wherein the first parameters depend on a bin response function.

10. The method according to claim 5, wherein the second parameters are related to pileup correction terms.

11. The method according to claim 4, further comprising:
(3) repeating, using each of the plurality of slabs, (1) for different current intensities other than the initial current intensity and at the same tube voltage, to obtain a universal table of estimated second parameters which are dependent on total counts of all energy bins based on the first parameters, in the entire current intensity range;
(4) performing a basis material decomposition in object/patient scans to estimate the basis material based on the first and the second parameters for combined counts of the sub-pixel pattern of (1).

12. The method according to claim 11, wherein the combining comprises summing performed over the entire sub-pixel pattern.

13. The method according to claim 11, wherein the combining comprises summing performed over a row direction or a channel direction of the sub-pixel pattern.

14. The method according to the claim 11, further comprising:
assessing image quality of a projection image by performing a phantom scan using the first parameters and the second parameters and if the quality of the projection image satisfies predefined standards, the first parameters and the second parameters are used for the material decomposition in object/patient scans to estimate the basis material.

15. The method according to claim 1, wherein the combining comprises averaging over an entire sub-pixel pattern and applying a normalization factor, based on an estimate of anti-scatter grid (ASG) shadow on the sub-pixel pattern, on the averaged counts.

16. The method according to claim 1, wherein the combining comprises averaging over a row direction or a channel direction of a sub-pixel pattern and applying a normalization factor, based on an estimate of anti-scatter grid (ASG) shadow on the sub-pixel pattern, on the averaged counts.

17. A photon counting computed tomography apparatus comprising:
a photon counting detector comprising a plurality of macro pixels, each macro-pixel including a plurality of micro pixels; and
processing circuitry configured to:
acquire calibration data based on the micro pixels,
generate combined calibration data which corresponds to spatial resolutions based on the obtained calibration data based on the micro pixels, the generated combined calibration data transformed to digital data, and
calibrate a detector response of the photon counting detector in response to the spatial resolutions based on the generated combined calibration data.

18. The photon counting computed tomography apparatus according to claim 17, wherein
the combined calibration data is generated by summing or averaging the calibration data based on the micro pixels.

19. The photon counting computed tomography apparatus according to claim 18, wherein
the summing or averaging is performed over the entire macro pixel.

20. The photon counting computed tomography apparatus according to claim 18, wherein
the summing or averaging is performed over a row direction or a channel direction of the macro pixel.

* * * * *